US006723322B1

(12) United States Patent
Lustigman et al.

(10) Patent No.: US 6,723,322 B1
(45) Date of Patent: Apr. 20, 2004

(54) **ANGIOGENIC *ONCHOCERCA VOLVULUS* PROTEINS AND USES THEREOF**

(75) Inventors: Sara Lustigman, New York City, NY (US); Eric Pearlman, Euclid, OH (US); Thomas R. Unnasch, Vestavia Hills, AL (US)

(73) Assignees: New York Blood Center, Inc., New York, NY (US); Case Western Reservei University, Cleveland, OH (US); UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/541,759

(22) Filed: Apr. 3, 2000

(51) Int. Cl.[7] ........................ A61K 39/00; A61K 48/00; C12N 15/87

(52) U.S. Cl. ................................ 424/191.1; 424/265.1; 435/455; 514/44

(58) Field of Search ........................ 514/2, 44; 530/350; 435/455, 459; 424/191.1, 265.1

(56) References Cited

U.S. PATENT DOCUMENTS 5,851,999 A 12/1998 Ullrich et al.

OTHER PUBLICATIONS

Smith, et al., 1998, Tropical Medicine and Parasitology, Suppl., vol 39, 00. 418–21.*

Pearlman, et al, Investigative Opthamology and Visual Scienc, 1998, vol 39, pp. 1176–1182.*

Wang, J. et al. 2000 J. Biol. Chem. 275 (1): 507–513.*

Tawe et al (Jul. 2000, Mol Biochem Parasitol, vol. 109, pp. 91–99 Apr. 5, 2003.*

Bowie et al (Science, 1990, 247:1306–1310).*

Burgess et al (J of Cell Bio. 111:2129–2138, 1990).*

Lazar et al (Molecular and Cellular Biology, 1988, 8:1247–1252).*

Pearlman, et al., Investigative Opthamology and Visual Science, 1998, 37:1176–82.*

Orkin et al, Report and Recommendations of the Panel to Assess the NIH investment in Research on Gene Therapy, 1995.*

Marshall, Science, 1995, 269:1050–1055.*

Anderson, Nature, vol. 392, suppl. 1998, pp. 25–30.*

Inder, et al., Nature, vol. 389, 1997, pp. 239–242.*

Brown et al., A novel in vitro assay for human angiogenesis. Laboratory Investigation, 75(4):539–55, Oct. 1996.

Rosengart et al., Angiogenesis gene therapy: phase I assessment of direct intramyocardial administration of an adenovirus vector expressing VEGF121 cDNA to individuals with clinically significant severe coronary artery disease. Circulation, 100:468–74, Aug. 3, 1999.

Zaniboni, A., Suramin: The discovery of an old anticancer drug. Med. Oncol. & Tumor Pharmacother, 7(4):287–90, 1990.

Chakravarti et al., Characterization of native pathogenic antigens of Onchocerca volvulus: identification of high molecular mass protein antigens eliciting interstitial keratitis in a guinea pig model. Experimental Eye Research, 60(4):347–58, Apr. 1995.

Hall and Pearlman, Pathogenesis of onchocercal keratitis (river blindness). Clin. Microbiol. Rev., 12(3):445–53, Jul. 1999.

Smith et al., Vascular perfusion of Onchocerca volvulus nodules. Trop. Med. Parasitol., 39 (Suppl. IV):418–21, Dec. 1988.

* cited by examiner

*Primary Examiner*—Karen A. Canella
*Assistant Examiner*—Misook Yu
(74) *Attorney, Agent, or Firm*—Amster, Rothstein & Ebenstein LLP

(57) ABSTRACT

The present invention provides a method for inducing angiogenesis in a tissue, by contacting the tissue with an amount of Ov-ASP effective to induce angiogenesis in the tissue. The present invention further provides a method for screening for an anti-Ov-ASP factor, by contacting a factor of interest with Ov-ASP, and assessing the ability of the factor to inhibit angiogenic activity of Ov-ASP. Additionally, the present invention provides a method for inhibiting angiogenesis in a subject.

12 Claims, 7 Drawing Sheets

ANGIOGENIC *ONCHOCERCA VOLVULUS* PROTEINS AND USES THEREOF

STATEMENT OF GOVERNMENT INTEREST

This invention was made with government support under NIH Grant Nos. EY10320 and EY11373. As such, the United States government has certain rights in this invention.

BACKGROUND OF THE INVENTION

Angiogenesis refers to the process by which new capillary blood vessels are formed from existing microvessels, resulting in the development of a blood supply to a given area of tissue [23, 25]. It is one of the most pervasive and fundamentally essential biological processes encountered in mammalian organizations. In the healthy, adult human body, angiogenesis is a normal and important function that is critical in a variety of physiological settings, including chronic inflammation, embryonic development, reproduction, and wound healing [22, 29]. For example, angiogenesis occurs in the female reproductive system, in response to ovulation or gestation, and in the normal hair cycle [28]. Nevertheless, apart from the processes of wound healing and inflammation, angiogenesis virtually never occurs physiologically in adult tissues, except in the ovary, the endometrium, and the placenta [27].

When defective or uncontrolled, however, angiogenesis is also central to a number of pathological processes, including: abnormalities of wound healing in diseases such as diabetes and duodenal ulceration; chronic inflammatory disorders, such as rheumatoid arthritis, psoriasis, and periodontitis; dermatological conditions such as cutaneous malignancy, decubitus ulcers, hemangiomas, Kaposi's sarcoma, psoriasis, pyogenic granulomas, and warts; diseases of the eye, particularly diabetic retinopathy; and growth of solid tumors, both benign and malignant [22, 23, 25, 26]. The consequence of abnormal angiogenesis is either excessive or insufficient blood vessel growth. Ulcers, strokes, and heart attacks, for example, can result from the absence of angiogenesis normally required for natural healing, while excessive blood vessel proliferation may favor arthritis, blindness, and tumor growth and dissemination [29 ].

The angiogenic process is tightly regulated—in both time and space—by a variety of endogenous angiogenic and angiostatic factors. It is propelled by a mixture of growth factors and pro-angiogenic cytokines, and is moderated by a collection of inhibitors of neovascularization which interfere with steps in the angiogenic process [22, 30]. In angiogenesis, capillary sprouts are formed in response to pro-angiogenic factors. The sprouts then grow and develop, driven by endothelial cell migration and proliferation, and organize themselves into a ordendritic structure [24]. Angiogenic and anti-angiogenic molecules control the formation of new vessels via different mechanisms. Hypoxia and other ill-defined stimuli drive tumor, inflammatory, and connective tissue cells to generate angiogenic molecules, such as vascular endothelial growth factor, fibroblast growth factor, transforming growth factor beta, and platelet-derived growth factor. Natural and synthetic angiogenesis inhibitors, such as angiostatin, thalidomide, and thrombospondin, can repress angiogenesis [23]. Most, if not all, of the angiogenesis-dependent disease processes result from both the unrestricted production of normal or aberrant forms of pro-angiogenic mediators, and the relative deficiency in angiogenic-inhibitory molecules [22].

Processes which are necessary for new vessel formation, and which are regulated by angiogenic and anti-angiogenic molecules, include the migration and proliferation of endothelial cells from the microvasculature, the controlled expression of proteolytic enzymes, the breakdown and reassembly of extracellular matrix, and the morphogenic process of endothelial tube formation. In animal models, some angiogenesis-dependent diseases can be controlled or modulated via induction or inhibition of new vessel formation [23]. The manipulation of new vessel formation, particularly the therapeutic induction of angiogenesis, would be desirable, as it would present new therapeutic options for treating a vast array of angiogenesis-dependent diseases or conditions, including cancer, diabetic retinopathy, inflammatory diseases, ischemic heart disease, myocardial infarction, peripheral vascular disease, and wound healing.

Onchocerciasis, or River Blindness, occurs primarily as a result of a host inflammatory response to infection with the filarial nematode *Onchocerca volvulus* (*O volvulus*). Transmitted by the bites of blackflies from the family Simuliidae, which breed in swiftly flowing streams, the parasite invades the skin, subcutaneous tissues, and other tissues, producing fibrous nodules. The host inflammatory response to infection with *O volvulus* may manifest in chronic skin disease and eye lesions. In the cornea, for example, this response produces neovascularization—the seminal event in the pathologic response process—followed by corneal opacification. Ocular onchocerciasis is characterized by lesions of the anterior eye, including punctate keratitis, deformation of the pupil, and an ingrowth of fibrovascular scar tissue that may result in blindness. In fact, onchocerciasis is the second leading cause of infectious blindness in the world. Of the 18 million people who are believed to be infected with onchocerciasis, approximately 270,000 are blind, and a further 500,000 are visually impaired [1–4, 31].

A library of expressed sequence tags of *O. volvulus* has recently been developed by the Filarial Genome Project, and numerous cDNAs have been cloned [5]. From this library, a number of *O. volvulus* proteins, including Ov20 [32], OvPDI [11], and Ovzf [33], have been characterized. However, the relationship between proteins of *O. volvulus* and the host inflammatory response in ocular onchocerciasis—particularly in the induction of corneal neovascularization—has not been fully delineated.

SUMMARY OF THE INVENTION

The present invention is based on the discovery that certain members of the Ov-ASP protein family are involved in the pathologic process of corneal neovascularization in animals infected with *O. volvulus*. This discovery, which indicates a pro-angiogenic role for Ov-ASP proteins, will have implications for wound healing and for the treatment of diseases, such as ischemia, where the enhancement or promotion of angiogenesis is desirable. In addition, this discovery permits screening for anti-Ov-ASP factors which inhibit or reduce the angiogenic activity of Ov-ASP. This finding will have implications in the treatment of ocular onchocerciasis.

Accordingly, the present invention provides a method for inducing angiogenesis in a tissue by contacting the tissue with an amount of Ov-ASP effective to induce angiogenesis in the tissue. The present invention further provides a method for screening for an anti-Ov-ASP factor, by contacting a factor of interest with Ov-ASP, and then assessing the ability of the factor to inhibit angiogenic activity of Ov-ASP. Finally, the present invention provides a method for inhibiting angiogenesis in a subject.

Additional objects of the present invention will be apparent in view of the description which follows.

DETAILED DESCRIPTION OF THE INVENTION

Figure 1:
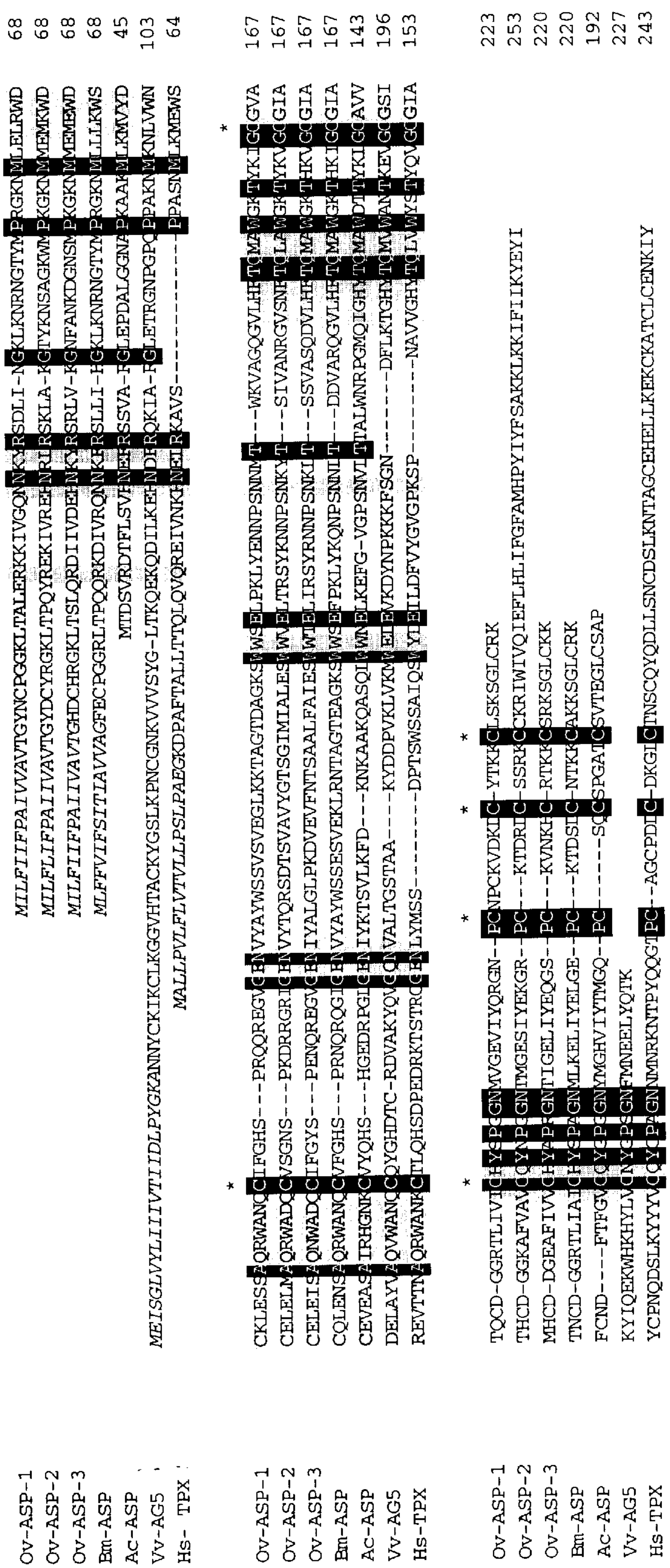
FIG. 1 presents a comparison between members of the Ov-ASP family and other members of the Tpx and CRISP families of protein. Sequences were aligned using the MACAW program, as described in Materials and Methods. Grey shading highlights areas with high mean similarity scores, while black shading highlights identical amino acids. Italics highlight the putative signal sequences identified, as described in Material and Methods. Asterisks highlight the conserved cysteine residues discussed in the text. Ov-ASP 1 (SEQ ID NO:1), Ov-ASP-2 (SEQ ID NO:2), and Ov-ASP-3 (SEQ ID NO:3)=members of the Ov-ASP family; Bm-ASP (SEQ ID NO:4)=*Brugia malayi* ASP homologue (accession number AF042088); Ac-ASP (SEQ ID NO:5)=*A. caninum* secreted protein (carboxyl terminal=192 amino acids; accession number Q16937); Vv-Ag5 (SEQ ID NO:6)=*Vespula vulgarus* antigen 5 (accession number Q05110); and Hs-Tpx (SEQ ID NO:7)=*Homo sapiens* Tpx protein (accession number P16562).

The present invention is directed to a method for inducing angiogenesis in a tissue, comprising contacting the tissue with an amount of Ov-ASP effective to induce angiogenesis in the tissue. As used herein, the term "Ov-ASP" is used to refer to members of the Ov-ASP protein family and analogues thereof, as well as homologues from other species which induce angiogenesis. Members of the Ov-ASP protein family include Ov-ASP-1, Ov-ASP-2, and Ov-ASP-3. Analogues of Ov-ASP include, for example, a functional variant of wild-type Ov-ASP protein which has Ov-ASP biological activity, as well as a fragment of Ov-ASP having Ov-ASP biological activity. As further used herein, the term "Ov-ASP biological activity" refers to Ov-ASP activity which induces angiogenesis.

In accordance with the methods of the present invention, the contacting of tissue with Ov-ASP may be effected by introducing a nucleic acid encoding Ov-ASP in a manner permitting expression of the Ov-ASP protein, or by introducing the Ov-ASP protein itself. The method of the present invention may also be used to induce angiogenesis in vivo or in vitro.

Tissue may be contacted with Ov-ASP by introducing to the tissue a nucleic acid encoding Ov-ASP, in a manner permitting expression of Ov-ASP. Nucleic acid encoding Ov-ASP may be genomic DNA or cDNA. The nucleic acid may be introduced using conventional procedures known in the art, including, without limitation, electroporation, DEAE Dextran transfection, calcium phosphate transfection, monocationic liposome fusion, polycationic liposome fusion, protoplast fusion, creation of an in vivo electrical field, DNA-coated microprojectile bombardment, injection with recombinant replication-defective viruses, homologous recombination, gene therapy, viral vectors, naked DNA transfer, or a combination thereof. It is to be appreciated by one skilled in the art that any of the above methods of DNA transfer may be combined.

A nucleic acid encoding Ov-ASP may be introduced to a tissue or subject using gene therapy, e.g., by introducing a recombinant vector containing a nucleic acid sequence encoding Ov-ASP. The nucleic acid sequence may be, for example, genomic DNA or cDNA. The recombinant vector containing nucleic acid encoding Ov-ASP may be administered to a subject using any number of procedures known to one skilled in the art, including, without limitation, electroporation, DEAE Dextran transfection, calcium phosphate transfection, monocationic liposome fusion, polycationic liposome fusion, protoplast fusion, creation of an in vivo electrical field, DNA-coated microprojectile bombardment, injection with recombinant replication-defective viruses, homologous recombination, gene therapy, viral vectors, naked DNA transfer, or a combination thereof. It is to be appreciated by one skilled in the art that any of the above methods of DNA transfer may be combined.

The recombinant vector may comprise a nucleic acid of, or corresponding to at least a portion of, the genome of a virus, where this portion is capable of directing the expression of a nucleic sequence encoding Ov-ASP, operably linked to the viral nucleic acid and capable of being expressed as a functional gene product in the tissue or subject. Recombinant viral vectors suitable for gene therapy may be derived from a variety of viral nucleic acids known to one skilled in the art, including, without limitation, the genomes of retrovirus, HSV, adenovirus, adeno-associated virus, Semiliki Forest virus, cytomegalovirus, vaccinia virus, and DNA and RNA viruses.

The recombinant vectors may also contain a nucleotide sequence encoding suitable regulatory elements so as to effect expression of the vector construct in a suitable host cell. As used herein, "expression" refers to the ability of the vector to transcribe the inserted DNA sequence into mRNA, so that synthesis of the protein encoded by the inserted nucleic acid can occur. Those skilled in the art will appreciate that a variety of enhancers and promoters are suitable for use in the constructs of the invention, and that the constructs will contain the necessary start, termination, and control sequences for proper transcription and processing of the nucleic acid sequence encoding Ov-ASP when the recombinant vector construct is introduced into a subject. Vectors suitable for the expression of the nucleic sequence encoding Ov-ASP are well known to one skilled in the art.

Suitable promoters include, but are not limited to, constitutive promoters, tissue specific promoters, and inducible promoters. Expression of the nucleic acid sequence encoding Ov-ASP may be controlled and affected by the particular vector into which the nucleic acid sequence has been introduced. Some eukaryotic vectors have been engineered so that they are capable of expressing inserted nucleic acids to high levels within the target cell. Such vectors utilize one of a number of powerful promoters to direct the high level of expression. Eukaryotic vectors use promoter-enhancer sequences of viral genes, especially those of tumor viruses. A particular embodiment of the invention provides for regulation of expression of the nucleic acid sequence encoding Ov-ASP using inducible promoters. Non-limiting examples of inducible promoters include, but are not limited to, metallothionine promoters and mouse mammary tumor virus promoters. Depending on the vector, expression of the nucleic acid sequence encoding Ov-ASP would be induced in tissue of a subject by the addition of a specific compound at a certain point in the growth cycle of the cells of the subject. Other examples of promoters and enhancers effective for use in the recombinant vectors include, but are not limited to, CMV (cytomegalovirus), SV40 (simian virus 40), HSV (herpes simplex virus), EBV (epstein-barr virus), retroviral, adenoviral promoters and enhancers, and tumor cell specific promoters and enhancers.

For the purposes of gene transfer into a tissue or subject, a recombinant vector containing nucleic acid encoding Ov-ASP may be combined with a sterile aqueous solution which is preferably isotonic with the blood of the recipient. Such formulations may be prepared by suspending the recombinant vector in water containing physiologically compatible substances such as sodium chloride, glycine, and the like, and having buffered pH compatible with physiological conditions to produce an aqueous solution, and rendering such solution sterile. In a preferred embodiment of the invention, the recombinant vector is combined with a 20–25% sucrose in saline solution in preparation for introduction into a subject.

It is within the confines of the present invention that the nucleic acid encoding Ov-ASP may be introduced into suitable cells in vitro using conventional procedures. Cells expressing Ov-ASP may then be introduced into tissue of a subject in order to induce angiogenesis. To reduce rejection, the cells are preferably removed from the subject, subjected to DNA techniques to incorporate the nucleic acid encoding Ov-ASP, and then reintroduced into the subject.

Nucleic acid encoding Ov-ASP, or nucleic acid encoding Ov-ASP contained in a vector, is introduced to tissue of a subject in an amount effective to induce angiogenesis in the tissue. However, the exact dosage will depend on such factors as the purpose of administration, the mode of administration, and the efficacy of the composition, as well as the individual pharmacokinetic parameters of the subject. Such therapies may be administered as often as is necessary, and for the period of time determined necessary by one skilled in the art.

In the method of the present invention, tissue may also be contacted with Ov-ASP by introducing to the tissue an Ov-ASP protein. The Ov-ASP protein may be produced synthetically or recombinantly, or may be isolated from native cells; however, it is preferably produced recombinantly, using cDNA encoding Ov-ASP (Ov-asp-1: GenBank accession number AF020586; Ov-asp-2: GenBank accession number H39490; and Ov-asp-3: GenBank accession number AA917267), along with conventional techniques. As used herein, the Ov-ASP-1, Ov-ASP-2, and Ov-ASP-3 proteins have the amino acid sequences set forth in FIG. 1.

The Ov-ASP protein may be introduced to tissue of a subject in vivo by known techniques used for the introduction of proteins, including, for example, injection, transfusion, or topical application. Injection or transfusion of Ov-ASP may be effected, for example, intradermally, intramuscularly, intraperitoneally, intravenously, or subcutaneously. When tissue in a subject is localized to a particular portion of the subject's body, it may be desirable to introduce the protein directly to the tissue by site-directed injection to a specific organ, or by some other means (e.g., by introducing Ov-ASP into the blood or another body fluid). The amount of Ov-ASP protein to be used is an amount effective to induce angiogenesis, and may be readily determined by the skilled artisan.

The ability of Ov-ASP to induce neovascularization renders Ov-ASP particularly useful for treating subjects suffering from diseases or conditions associated with a need for angiogenesis. The subject is preferably a mammal (e.g., humans, domestic animals, and commercial animals), and is most preferably a human. It is believed that, by inducing angiogenesis, Ov-ASP will be useful for the treatment of diseases or conditions where the enhancement or promotion-of angiogenesis is desirable. It is further believed that Ov-ASP would be effective either alone or in combination with therapeutic agents (e.g., chemotherapeutic agents or antiviral agents) or angiogenic factors (e.g., agents which induce, enhance, or promote angiogenesis) used in the treatment of these diseases or conditions.

Non-limiting examples of tissues into which Ov-ASP may be introduced to induce angiogenesis include cardiac, cerebrovascular, endothelial, epithelial, fibrous, muscular, transplanted, vascular, vesicular, and wounded tissues. Transplanted tissues are, for example, heart, liver, lung, kidney, and ocular tissues. The tissues into which Ov-ASP may be introduced to induce angiogenesis further include those associated with diseases or conditions where the induction or promotion of angiogenesis would be desirable, including, without limitation, circulatory disorders, congenital heart disease, ischemia, myocardial disease, myocardial ischemic disorders, organ transplantation, pericardial disease, skin grafts, and vascular disorders. Examples of ischemia include, without limitation, cerebrovascular ischemia, myocardial ischemia, and veno-occlusive disease. An example of myocardial ischemia is coronary artery disease.

The present invention is based on the discovery that Ov-ASP induces angiogenesis. Accordingly, Ov-ASP may be used accelerate or enhance various biological processes associated with angiogenesis. For example, Ov-ASP may be administered to enhance wound healing and organ transplantation, including the transplantation of artificial organs. Therefore, this invention is directed to a method of enhancing wound healing in a subject by administering Ov-ASP, and to a method of enhancing organ transplantation in a subject by administering Ov-ASP. In addition, Ov-ASP may be used to accelerate endothelial cell coverage of vascular grafts in order to prevent graft failure due to reocclusion. It may also be administered to enhance skin grafting. Thus, this invention is further directed to a method for accelerating endothelial cell coverage of vascular grafts in a subject by administering Ov-ASP, and to a method for enhancing skin grafting in a subject by administering Ov-ASP. Ov-ASP, in the form of a nucleic acid, a recombinant vector containing nucleic acid encoding Ov-ASP, or a protein, may be administered according to the various methods of introduction, and in the various amounts, described above.

The present invention also provides a method for screening for an anti-Ov-ASP factor. An "anti-Ov-ASP factor" is a natural or synthetic agent which antagonizes Ov-ASP by reducing or inhibiting Ov-ASP biological activity (i.e., Ov-ASP angiogenic activity). It is also within the confines of the present invention that an anti-Ov-ASP factor is a natural or synthetic agent which antagonizes other angiogenic factors (e.g., agents which induce, enhance, or promote angiogenesis), including analogues and homologues of Ov-ASP, by reducing or inhibiting their angiogenic activity. The anti-Ov-ASP factor may be in the form of an antibody, a Fab fragment, an $F(ab')_2$ fragment, a peptide, a polypeptide, a protein, and any combinations thereof. A Fab fragment is a univalent antigen-binding fragment of an antibody, which is produced by papain digestion. An $F(ab')_2$ fragment is a divalent antigen-binding fragment of an antibody, which is produced by pepsin digestion. For example, the anti-Ov-ASP factor may be an antibody reactive with Ov-ASP. Alternatively, the anti-Ov-ASP factor may be an enzyme reactive with Ov-ASP. As used herein, "reactive" means the anti-Ov-ASP factor has affinity for, binds to, or is directed against Ov-ASP.

As used herein, the antibody of the present invention may be polyclonal or monoclonal, and may be produced by techniques well known to those skilled in the art. Polyclonal antibody, for example, may be produced by immunizing a mouse, rabbit, or rat with purified Ov-ASP. Monoclonal antibody may then be produced by removing the spleen from the immunized mouse, and fusing the spleen cells with myeloma cells to form a hybridoma which, when grown in culture, will produce a monoclonal antibody. The antibody of the present invention also includes a humanized antibody, made in accordance with procedures known in the art.

An anti-Ov-ASP factor may be screened using in vitro assays. In the method of the present invention, an anti-Ov-ASP factor may be screened by contacting a factor of interest with Ov-ASP, then assessing the ability of the factor to inhibit angiogenic activity of Ov-ASP. For example, a corneal assay may be used to screen for an anti-Ov-ASP factor. An agent of interest may be brought into contact with corneal tissue or cells containing Ov-ASP, then the corneal tissue or cells may be assessed to determine if the agent of interest reduces or inhibits angiogenesis or neovascularization in the corneal tissue or cells. Additionally, employing a similar procedure, an in vitro assay using human vascular endothelial cells or human umbilical vein endothelial cells (HUVECs) may be utilized to screen for an anti-Ov-ASP factor. An anti-Ov-ASP factor identified by the above-described screening method is also provided by the present invention.

The present invention further provides a method for inhibiting angiogenesis in a subject. The method of the present invention comprises administering to a subject an amount of anti-Ov-ASP factor effective to inhibit angiogenesis in the subject. The amount of anti-Ov-ASP factor required to inhibit angiogenesis may be readily determined by one skilled in the art. The present method for inhibiting angiogenesis in a subject would be useful for treating a subject having a disease or condition where the inhibition of angiogenesis would be desirable, including, without limitation, arthritis, corneal disease, diabetic retinopathy, pyogenic granulomas, hypertrophic scars, inflammation, Kaposi's sarcoma, liver cirrhosis, benign neoplasia (e.g., hemangiomas), malignant neoplasia (e.g., skin cancer, cutaneous malignancies, and other malignancies), onchocerciasis, psoriasis, growth of solid tumors, metastatic spread of solid tumors, and warts. The anti-Ov-ASP factor may be administered in an amount which is effective to inhibit angiogenesis n the subject. This amount may be readily determined by the skilled artisan.

The present invention further provides a pharmaceutical composition comprising an anti-Ov-ASP factor and a pharmaceutically-acceptable carrier. The pharmaceutically-acceptable carrier must be "acceptable" in the sense of being compatible with the other ingredients of the composition, and not deleterious to the recipient thereof. Examples of acceptable pharmaceutical carriers include carboxymethyl cellulose, crystalline cellulose, glycerin, gum arabic, lactose, magnesium stearate, methyl cellulose, powders, saline, sodium alginate, sucrose, starch, talc, and water, among others. Formulations of the pharmaceutical composition may conveniently be presented in unit dosage. The formulations may be prepared by methods well-known in the pharmaceutical art. For example, the active compound may be brought into association with a carrier or diluent, as a suspension or solution. Optionally, one or more accessory ingredients (e.g., buffers, flavoring agents, surface active agents, and the like) may also be added. The choice of carrier will depend upon the route of administration. The pharmaceutical composition would be useful for administering the anti-Ov-ASP factor to a subject to treat a disease or condition where the inhibition of angiogenesis would be desirable, including, without limitation, benign neoplasia, malignant neoplasia, and onchocerciasis. Where the pharmaceutical composition is administered to a subject to inhibit angiogenesis, the anti-Ov-ASP factor is provided in an amount which is effective to inhibit angiogenesis in the subject. This amount may be readily determined by the skilled artisan.

The present invention is described in the following Experimental Details section, which is set forth to aid in the understanding of the invention, and should not be construed to limit in any way the scope of the invention as defined in the claims which follow thereafter.

EXPERIMENTAL DETAILS

1. Introduction

Ocular onchocerciasis (River Blindness) occurs primarily as a result of a host inflammatory response to dead and dying *Onchocerca volvulus* (*O. volvulus*) worms in the eye. In the cornea, this response is initially manifested in the development of new blood vessels (neovascularization), and later in the opacification of the cornea. Animal models have shown that development of *O. volvulus*-mediated corneal inflammation (keratitis) results from the temporal recruitment to the cornea of neutrophils and eosinophils, through the network of new blood vessels. The inflammatory process is dependent on development of a systemic T helper type 2 (Th2)-type response to the parasite antigens [1–4]. However, there is currently little understanding of the mechanisms by which the parasite is capable of inducing corneal neovascularization—the seminal event in the pathologic process.

Recently, the Filarial Genome Project began to develop a library of expressed sequence tags (ESTs) from *O. volvulus* [5]. One of the most abundant cDNAs identified in infective larvae encodes a protein that demonstrates a significant degree of similarity to the vespid venom antigen 5 [6], and to the major secreted protein of *Ancylostoma caninum* (*A. caninum*) infective larvae [7]. This protein was designated Ov-asp-1 (for *O. volvulus* Activation associated Secreted Protein).

Vespid venoms (bee and hornet venoms) are important allergens of humans. Furthermore, vespid venom antigen 5 has similarities to the testis-specific protein (Tpx)/cysteine-rich secreted protein (CRISP) families of proteins [8]. These families of proteins include a major autoantigen of the mammalian sperm acrosome, and are found in many other vertebrate tissues [8, 9].

Because the Ov-ASPs are similar to a component of vespid venoms, and vespid venoms are capable of inducing both allergic and inflammatory responses [10], it was hypothesized that these proteins may play a role in the development of ocular onchocerciasis. In the current study, the inventors present data demonstrating that two Ov-ASP proteins induce an angiogenic response in naive mouse corneas, thereby suggesting that these proteins may play a direct role in the pathogenesis of ocular onchocerciasis, possibly by promoting neovascularization during nodule formation.

2. MATERIALS AND METHODS

A. Cloning and Expression of the Ov-asp cDNAs

Previously, the inventors isolated a cDNA encoding one member of the Ov-ASP protein family by immunoscreening an L3 cDNA expression library (OvB93-RP, GenBank accession number AF020586). The isolated cDNA was designated Ov-asp-1. The complete nucleotide sequences of two other members of the Ov-asp family were identified as part of the *O. volvulus* EST sequencing project, and have been designated Ov-asp-$^2$ (GenBank accession number H39490) and Ov-asp-3 (GenBank accession number AA917267). The present inventors designed three sets of primers flanking the complete open reading frames of each of the clones with EcoR1 sites at their 5' ends to facilitate subsequent cloning. The nucleotide sequences of the primers were as follows:

Ov-asp-1 exp-f: 5'-GGAATTCCATATGATACT=TCATCATCTTC-3' (SEQ ID NO:8)

Ov-asp-1 exp-r: 5'-TCATTTTCTGCACAGTCCAGA-3' (SEQ ID NO:9)

Ov-asp-2 exp-f: 5'-GGATTCCATATGATACllICTCATCTTC-3' (SEQ ID NO:10)

Ov-asp-2 exp-r: 5'-CATAATAACTACTAAATATATACGT-3' (SEQ ID NO:11)

Ov-asp-3 exp-f: 5'-GGAATTCCATATGATACT=TrCATCATCTTC-3' (SEQ ID NO:12)

Ov-asp-3 exp-r: 5'-TCATITGCACAATCCAGA-3' (SEQ ID NO:13)

The primer pairs were used to amplify the corresponding cDNAs from an *O. volvulus* larval cDNA library (SAW94WL-OvL3). The amplification reactions were carried out in a total volume of 200 $\mu$l in a mixture containing 20 mM of Tris-HCl (pH 8.8), 2 mM of $MgSO_4$, 10 mM of KCl, 10 mM of $(NH_4)_2SO_4$, 0.1% Triton×100, 100 $\mu$g/ml of bovine serum albumin, 200 $\mu$M of dNTPs, 0.5 $\mu$M of each primer, 5 units of Taq DNA polymerase (Sigma Chemical, St. Louis, Mo.), and 2.5 units of Pfu DNA polymerase (Stratagene, LaJolla, Calif.). Cycling conditions consisted of an initial denaturation of 5 min at 95° C., followed by 40 cycles, each consisting of 45 sec at 95° C., 1 min at 50° C., and 1 min at 72° C. The reaction was completed with a final step consisting of 7 min at 72° C. The reaction products were cloned into the TA-cloning vector (Invitrogen, Carlsbad, Calif.) following the manufacturer's instructions. Individual clones containing the polymerase chain reaction (PCR) products were isolated, and their DNA sequences were determined to ensure that the amplification process did not introduce any mutations. Inserts from clones with correct sequences corresponding to the three Ov-ASP proteins were excised by digestion with EcoR1, and sub-cloned into the pMALCR1 expression vector (New England Biolabs, Beverly, MA). Production of recombinant maltose-binding protein (MBP) fusion proteins was induced in *E. coli* using 1 mM of IPTG. The fusion proteins were purified by amylose affinity chromatography, as previously described [11]. Yields from the Ov-ASP-1/MBP and Ov-ASP-2/MBP preparations were in the range of 1-2 mg of protein per liter, and the purified protein was 80–90% homogeneous, as judged by SDS PAGE (data not shown). Induced cultures expressing Ov-ASP-3/MBP did not produce a stable fusion protein.

B. Library Polymerase Chain Reactions

In order to investigate the expression pattern of the three Ov-asp transcripts, gene-specific primers were designed to amplify an approximately 400-bp fragment of the 3' region of each of the cDNA clones. Amplifications were also carried out employing primers for a cDNA encoding the glycolytic enzyme glyceraldehyde 3-phosphate dehydrogenase (Ov-gpd-1) as an internal control. The gene-specific primers used were:

Ov-asp-1-f: 5'-AAAACTGCTGGTACGGA-3' (SEQ ID NO:14)

Ov-asp-1-r: 5'-CGAGAATTAAATGAAGAAAAGCG-3' (SEQ ID NO:15)

Ov-asp-2-f: 5'-GTTTACACCCAGCGGTCAGATAC-3' (SEQ ID NO:16)

Ov-asp-2-r: 5'-CCAAAAATTAAATGAAGAAATTCAATI7GC-3' (SEQ ID NO:17)

Ov-asp-3-f: 5'-CGCCTTAGGGTTACCAAAAGATG-3' (SEQ ID NO:18)

Ov-asp-3-r: 5'-CAAAAATTAAATGAAGTGAAACG-3' (SEQ ID NO:19)

Ov-gpd-1-f: 5'-TGATCTCACTTGCCGACTGC-3' (SEQ ID NO:20)

Ov-gpd-1-r: 5'-AAGGTGTTGTCAGAAGGC-3' (SEQ ID NO:21)

PCR amplifications were carried out on 10 $\mu$l aliquots of each amplified *O. volvulus* cDNA library from microfilariae (mf) (SAW98MLW-OvMf), second-stage larvae (L2) (SAW98MLW-OvL2), third-stage larvae (L3) (SAW94WL-OvL3), molting third-stage larvae (mL3) (SL96MLW-OvmL3), forth-stage larvae (L4) [12], adult male (SAW98MLW-OvAM), and adult female [12], using the gene-specific primer pairs. Following an initial 5 min denaturation, 35 cycles of amplification were performed using Taq DNA polymerase (Promega, Madison, WI) under the following cycling conditions: 95° C. for 1 min, 50° C. for 1 min, and 72° C. for 1 min. PCR products were analyzed by agarose gel electrophoresis.

C. Southern Blots

Southern blots were prepared from BamHl and HindIII restricted human *O. volvulus* genomic DNA samples, as previously described [11]. The blot was sequentially probed with purified insert DNA from a clone encoding the Ov-asp-2 open reading frame, then with a purified DNA fragment encoding a portion of *O. volvulus* prolyl 4-hydroxylase. The blot probed with the Ov-asp-2 insert was washed under conditions of moderate stringency (0.4×SSC, 1% SDS, at 48° C.), while the blot hybridized with the *O. volvulus* prolyl 4-hydroxylase insert was washed at high stringency (0.2×SSC, 1% SDS, at 65° C.).

Signal sequences and putative cut sites were identified using the SignalP server, employing the method of von Heijne [13]. Peptide sequences were aligned using the Gibbs sampler algorithm of the MACAW program package [14]. Phylogenetic analyses were carried out on the aligned sequences using the branch and bound algorithm found in the PAUP program package [15]. The phylogenetic analysis was limited to the amino acids extending from position 24 to the end of the protein, to eliminate the putative signal sequences. Gaps introduced during the process of alignment were not considered as character states. Statistical support for the phylogeny was evaluated by bootstrap re-analysis of 1000 replicated data sets.

E. Assessment of Angiogenic Activity

The neovascular response in the corneas was determined by slit-lamp examination, using the method described by Kenyon et al. [16]. Briefly, corneas of 4- to 6-week-old BALB/c mice, obtained from Jackson Laboratories (Bar Harbor, Me.), were injected with 30 $\mu$g of each recombinant protein in 10 $\mu$l of sterile, endotoxin-free Hanks Buffered Salt Solution (Life Technologies, Gaithersburg, Md.). Growth of new vessels was quantified by measuring the vessel length from the limbus to the site of injection using a linear reticule, and by estimating the contiguous circumferential zone of neovascularization as "clock hours" (30° of arc=1 clock hour).

F. Histology

Eyes were removed, fixed overnight in 10% formaldehyde, processed by standard methods, and embedded in paraffin. Sections (5 $\mu$m) were stained with hematoxylin and eosin, and the presence of blood vessels in the corneas was determined by light microscopy.

3. Results

By immunoscreening an *O. volvulus* L3 cDNA library, the inventors previously isolated cDNA encoding a protein similar to the family of vespid allergen antigens. The *O. volvulus* EST sequencing initiative has also identified a number of distinct clones, with significant levels of homology to the antigen 5 proteins of vespid venoms [17], members of the Tpx and CRISP protein families, and a major secreted antigen of *Ancylostoma caninum* infective larvae [7]. These sequences have been grouped into a family of proteins designated Ov-ASP (for Onchocerca volvulus Activation associated Secreted Proteins). Full-length cDNAs, encoding the three members of the Ov-ASP family, were isolated by PCR amplification from a cDNA library prepared from *O. volvulus* infective larvae, as described in Materials and Methods. The derived amino acid sequences of the three members of the Ov-ASP family are presented in FIG. 1. All three proteins have characteristics similar to members of the Tpx and CRISP protein families. The Ov-ASPs are 54–62% identical to each other, and contain 6 of the 10 conserved cysteine residues found in the vertebrate members of the Tpx family of proteins. All three of the members of the Ov-ASP family contain putative signal sequences at their amino terminal ends. In addition, the three Ov-ASPs contain the sequence HFTQ, or a closely related variant (NFTQ), which is a conserved variation of the HYTQ sequence found in most members of the CRISP family [7].

Figure 2:
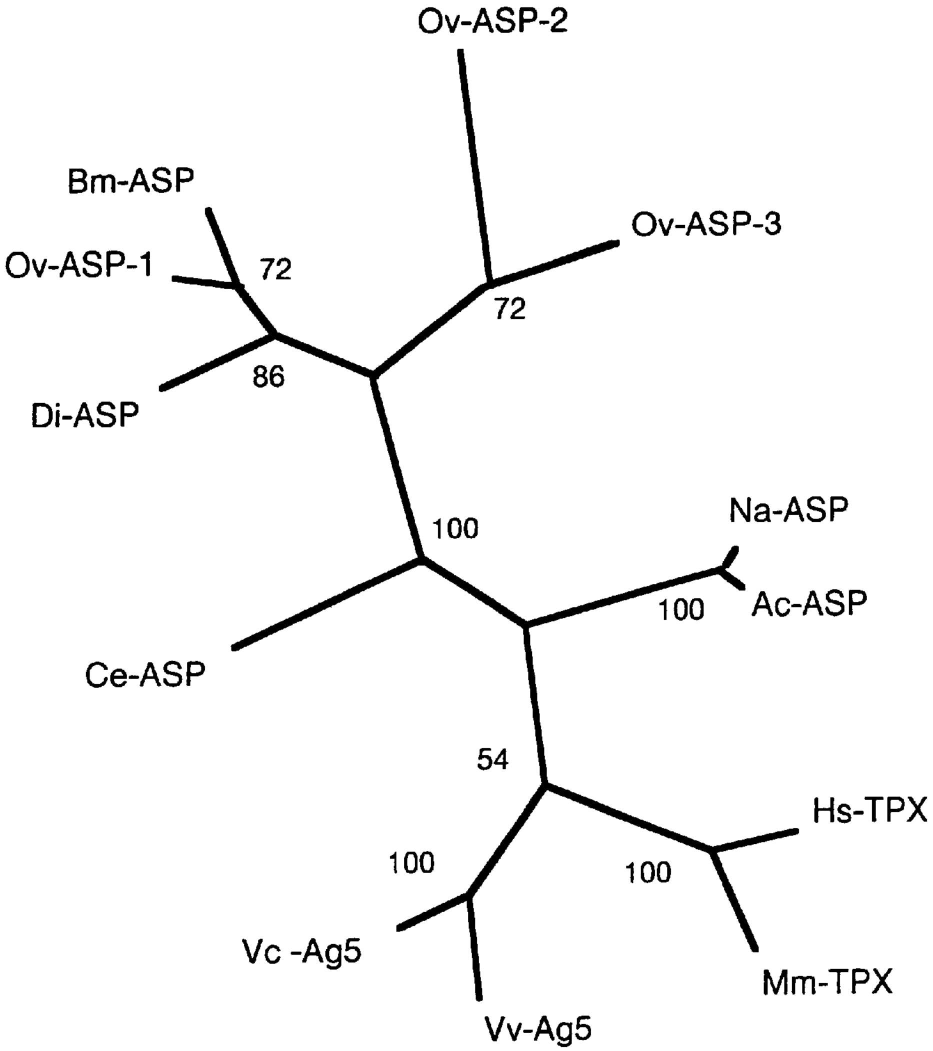
FIG. 2 depicts a phylogenetic analysis of members of the Ov-ASP family. The phylogeny shown was constructed as described in Materials and Methods. This analysis produced a single parsimonious tree, as shown here. Statistics for this phylogeny were as follows: tree length=759 (range 678–1071); consistency index=0.893; and rescaled consistency index=0.709. Numbers indicate bootstrap support values for the groups distal to the labeled node. Taxa are as follows: Ov-ASP-1, Ov-ASP-2, Ov-ASP-3=members of the Ov-ASP family; Bm-ASP=*Brugia malayi* ASP homologue (accession number AF042088); Di-ASP=*Dirofilaria immitis* ASP homologue (accession number AF001100); Ce-ASP=*Caenorhabditis elegans* ASP homologue (accession number CAA92136); Ac-ASP=*A. caninum* secreted protein (carboxyl terminal=192 amino acids; accession number Q16937); Na-ASP=*Necator americanus* homologue of ASP (carboxyl terminal=192 amino acids; accession number AF07952); Vv-Ag5=Vespula vulgarus antigen 5 (accession number Q05110); Vc-Ag5=Vespa crabro antigen 5 (accession number P35781); Hs-Tpx=Homo sapiens Tpx protein (accession number P16562); Mm-TPX=Mus musculus Tpx protein (accession number P16563)

When the phylogenetic relationship of the Ov-ASP proteins was examined, Ov-ASP-3 and Ov-ASP-2 formed a clade that was distinct from that formed by Ov-ASP-1 and the ASP homologues identified in other filarial parasites (*B. malayi* and *D. immitis*) (FIG. 2). Furthermore, the filarial ASPs formed a group that was distinct from the ASP homologues of other organisms, including the ASPs from *A. caninum* and *C. elegans*. These results suggested that the filarial ASPs represent a novel subfamily of CRISP proteins.

Figure 3:
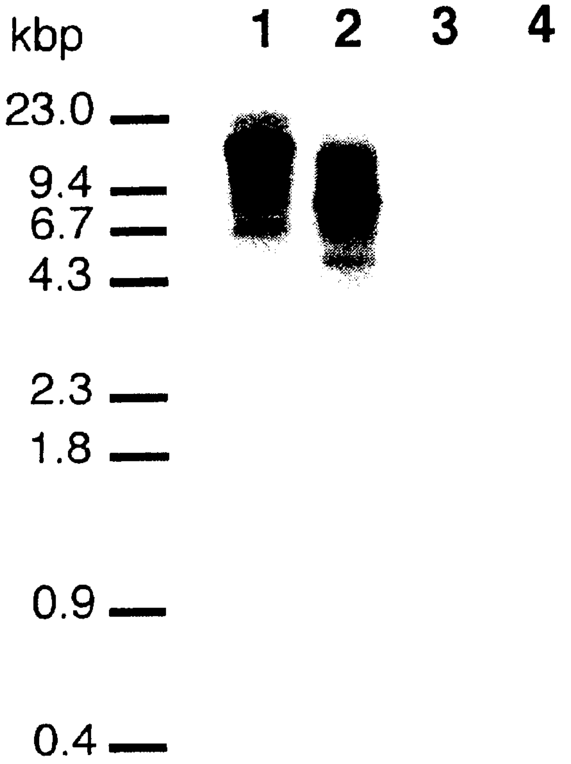
FIG. 3 provides a genomic Southern blot analysis of members of the Ov-ASP family. A genomic Southern blot was prepared with *O. vovulus* and human restriction-digested DNA was probed with a purified insert encoding the full-length open reading frame of Ov-asp-2, as described in Materials and Methods. Lane 1 =*O. vovulus* genomic DNA digested with BamHl; Lane 2=*O. volvulus* genomic DNA digested with HindIII; Lane 3=human genomic DNA digested with BamH1; and Lane 4=human genomic DNA digested with HindIII

The discovery of three distinct *O. volvulus* clones encoding homologues of the vespid antigens suggested that the Ov-asp clones are members of a multigene family. To explore the structure of this family in more detail, a Southern blot prepared from *O. volvulus* genomic DNA was probed under conditions of moderate stringency with a purified insert encoding the Ov-asp-2 open reading frame. The Ov-asp-2 cDNA hybridized to a large number of DNA bands in both Hindll1 and BamHl restricted *O. volvulus* DNA, ranging in size from 3.5 to 16 kbp (FIG. 3). In contrast, no hybridization to human genomic DNA was detected (FIG. 3). When the blot was re-probed with a gene sequence known to be present as a single copy in the *O. volvulus* genome (the *O. volvulus* prolyl 4-hydroxylase alpha subunit I), single distinct bands were detected in both *O. volvulus* lanes, confirming that the multiple bands seen were not artifacts produced either by partial digestion or degradation of the genomic DNA samples used to prepare the Southern blot (data not shown). These results, when taken together, suggest that the Ov-asps comprise a multigene family within the *O. volvulus* genome.

Figure 4:
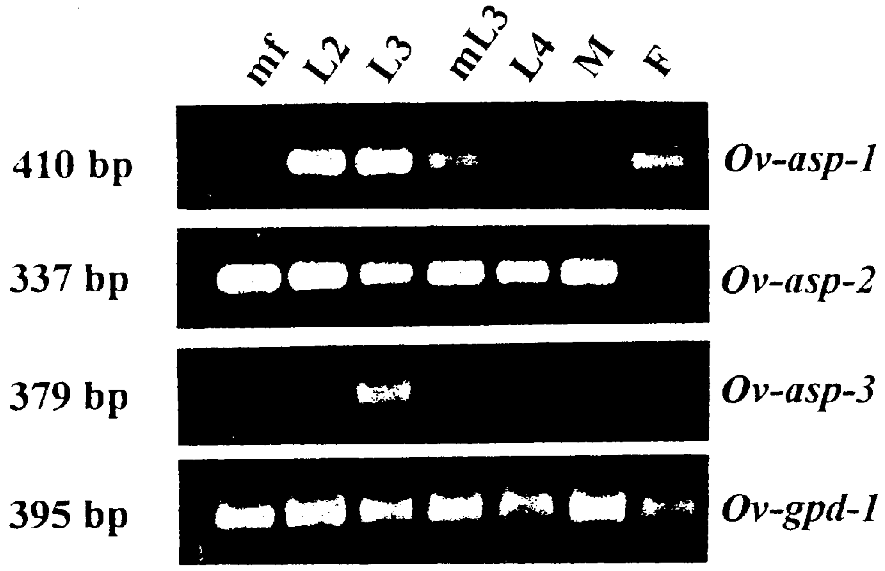
FIG. 4 illustrates stage-specific PCR showing expression profiles of the three *O. volvulus* asp genes in different stages of the life cycle. Amplifications were carried out using gene-specific primers on cDNA libraries prepared from microfilariae (mf), second-stage larvae (L2), third-stage larvae (L3), molting larvae (mL3), fourth-stage larvae (L4), and adult male and female. The *O. Volvulus* gene encoding glyceraldehyde 3-phosphate dehydrogenase (Ov-gpd-1) was included as an internal control.

To gain some insight into the developmental profile of expression of the three members of the Ov-asp family, non-quantitative, stage-specific PCR analyses were performed using primers specific for each of the three members of the Ov-asp family; cDNA libraries derived from various life stages of the parasite were used as template DNA. The Ov-asp-2 transcript was found to be present in all stages, while the Ov-asp-3 was L3 stage-specific, and the Ov-asp-1 transcript was confined to the L2, L3, mL3, and adult female stages (FIG. 4). A search of the 4,635 L3 and mL3 ESTs in the *O. volvulus* EST database (as of 1999), using gene-specific segments of the three Ov-asp cDNAs, showed that the Ov-asp-3 is L3-specific, while the Ov-asp-1 and the Ov-asp-2 are both present in the mL3, and up-regulated in the L3 stage (Table 1). The Ov-asp gene cluster comprises up to 0.81% of the L3/mL3 ESTs in the current *O. volvulus* EST database. Transcripts of Ov-asp-1 and Ov-asp-2 could be amplified from other life stages of the parasite, but no corresponding ESTs were identified in the present EST data sets of any other stage (mf, L2, male, female). Taking into account the relatively smaller number of ESTs in these data sets, these results suggest that the Ov-asp-1 and Ov-asp-2 transcripts are probably down-regulated in these stages.

TABLE 1

Distribution of the three Ov-asp ESTS within the *O. volvulus* larval EST sequence data sets

| | L3 | mL3 |
|---|---|---|
| Ov-asp-1 | 29 | 2 |
| Ov-asp-2 | 11 | 2 |
| Ov-asp-3 | 7 | 0 |

Figure 5:
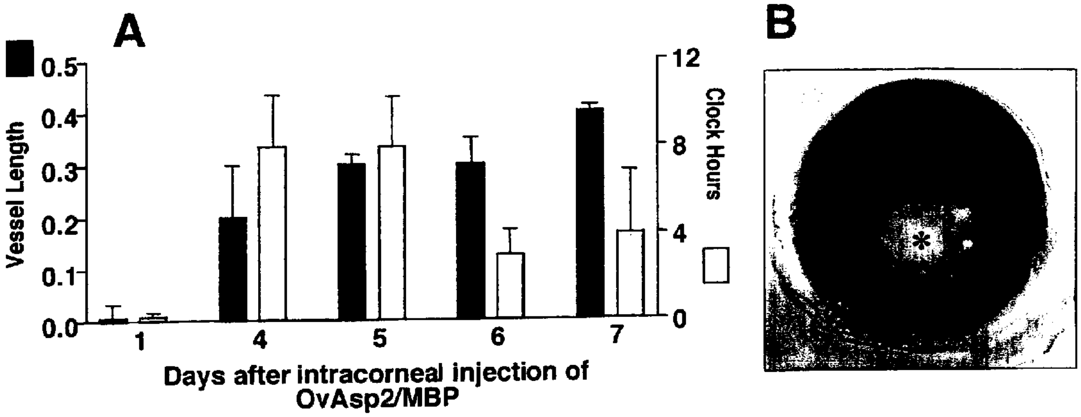
FIG. 5 depicts an angiogenic response elicited by Ov-ASP-2. Panel A: Thirty μg of Ov-ASP-2/MBP was injected into the corneal stroma of BALB/c mice. Growth of blood vessels was monitored by length (vessel length) and by circumferential area (clock hours) from the injection site over time, as described in Materials and Methods. Data are means ±S.D. of 5 mice per group. This experiment was repeated 5 times with similar results. Panel B: Photomicrograph of BALB/c mouse, 7 days after injection of Ov-ASP-2/MBP. The asterisk indicates the site of injection.

The two major clinical features of anterior ocular onchocerciasis are corneal opacification and neovascularization [1]. To determine if the Ov-ASPs are capable of directly inducing either of these features, Ov-ASP-1 and Ov-ASP-2 were expressed in *E. coli* as soluble fusion proteins with maltose-binding protein (MBP), and purified to homogeneity by amylose affinity chromatography. Thirty μg of each purified protein were injected into the corneas of naive BALB/c mice, and growth of blood vessels was monitored by slit-lamp examination. As shown in FIG. 5, the Ov-ASP-2/MBP construct induced a pronounced angiogenic response, with vessels growing from the peripheral cornea to the site of injection. Vessel length was maintained throughout the 7-day period, although the area of the cornea in which vessels were present (measured as clock hours) decreased after 5 days. Similar kinetics were found after injection of 10 μg of protein (data not shown).

Figure 6:
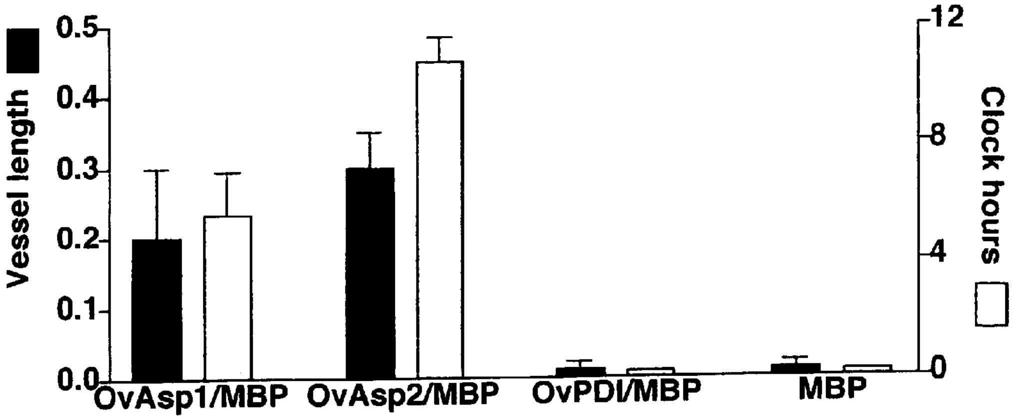
FIG. 6 demonstrates the specificity of the angiogenic response elicited by Ov-ASP/MBP fusion proteins. BALB/c mice were injected in the corneal stroma with Ov-ASP-1/MBP, Ov-ASP-2/MBP, Ov-PDI/MBP, or MBP alone. Results shown are from day 3 after injection, and represent means ±S.D. of 5 mice per group. This experiment was repeated 5 times with similar results.

To ascertain the specificity of the angiogenic response, mice were injected with Ov-ASP-1/MBP, Ov-ASP-2/MBP, MBP alone, or with *O. volvulus* protein disulfide isomerase fused with MBP (Ov-PDI/MBP) [18]. As shown in FIG. 6, angiogenesis developed in animals injected with Ov-ASP-1/MBP or Ov-ASP-2/MBP, but not in animals injected with MBP alone or Ov-PDI/MBP. This result indicates that the angiogenic response was specific for the Ov-ASP proteins.

Figure 7:
FIG. 7 depicts the histology of mouse cornea, 7 days after injection of Ov-ASP-2/MBP. Numerous blood vessels are present in the corneal stroma (large arrows), but only occasional mononuclear cells (small arrows) are present. The micrograph is representative of 5 animals per group, and 5 replicated experiments.

To determine if the angiogenic response induced by the Ov-ASP/MBP proteins was associated with the presence of host inflammatory cells, eyes of mice injected with Ov-ASP-2/MBP or the control proteins were removed, then fixed in formalin. Paraffin sections (5 pm) were examined after staining with hematoxylin and eosin. Corneas of Ov-ASP-2/MBP-injected animals had numerous blood vessels, but relatively few inflammatory cells (FIG. 7). In contrast to the model of *O. volvulus* keratitis in which there is an intense neutrophilic and eosinophilic infiltrate [1], most of the inflammatory cells in Ov-ASP-2/MBP-injected corneas were mononuclear. Similar results were seen after injection of Ov-ASP-1/MBP, whereas no vessels or inflammatory cells were detected in the corneas of animals injected with Ov-PDI/MBP or MBP alone (data not shown).

4. Discussion

One of the most abundant larval cDNAs identified by EST analysis encodes a member of the Ov-ASP family. The identification of three members of the Ov-ASP family, together with the genomic Southern blot data presented above, suggest that the Ov-ASPs constitute a multi-gene family with several members. Furthermore, the three members of the Ov-ASP family characterized to date appear to exhibit different developmental profiles, suggesting that these proteins have distinct functions in the parasite. The biological function of the vespid venom homologues in invertebrates and in *A. caninum* remains obscure. However, the *A. caninum* homologue is a major secreted protein in activated infective larvae, suggesting that this protein plays an important role in the establishment of infection [7].

Apart from the Ov-ASP homologues, none of the individual recombinant *O. volvulus* proteins tested to date has elicited any response in naive animals in the established mouse model for ocular onchocerciasis [18, 19]. The response induced by Ov-ASP-1/MBP and Ov-ASP-2/MBP also differed significantly from that seen in animals immunized subcutaneously and challenged intrastromally with soluble native parasite antigens—a procedure that induces severe corneal opacification [3, 18]. In immunized animals challenged intracorneally with total *O. volvulus* antigens, there was a pronounced migration of eosinophils and neutrophils into the cornea and severe edema in contrast, injection of the naive animals with Ov-ASP-1/MBP or Ov-ASP-2/MBP resulted in a minimal inflammatory response. These data suggest that Ov-ASP proteins may directly induce an angiogenic response and may therefore contribute to corneal neovascularization in onchocercal keratit is.

The mechanisms by which members of the Ov-ASP protein family stimulate new blood-vessel formation in the corneas of naive animals have yet to be determined. However, it is possible to envisage at least two mechanisms by which this may occur: (1) the Ov-ASPs may directly stimulate the growth of vascular endothelial cells to proliferate and to form new blood vessels; (2) alternately, angiogenesis may be due to the release of endothelial cell growth factors produced by infiltrating mononuclear cells.

Although corneal neovascularization is important in the development of ocular pathology associated with *O. volvulus* infection, angiogenesis may also be essential for maintaining the nodule in which the adults reside. These nodules are highly vascularized [20]; their survival may depend on production of angiogenic proteins in a manner similar to that described for tumors [21]. It may be that one function of the members of the Ov-ASP family is to promote neovascularization during nodule formation, thereby ensuring a sufficient blood supply to the adult parasite. The potential importance of the members of the Ov-ASP protein family in establishing infection by the infective larvae, and in supporting the development of the nodule by the juvenile adult parasite, suggests that these proteins may be a potential target for immunotherapeutic or chemotherapeutic attack against *O. volvulus* infection.

References

1. Hall and Pearlman, Pathogenesis of onchocercal keratitis (river blindness). *Clin. Micro. Rev.*, 12:445–53, 1999.
2. Pearlman et al., Interleukin 4 and T helper type 2 cells are required for development of experimental onchocercal keratitis (river blindness). *J. Exp. Med.*, 182:931–40, 1995.
3. Pearlman, E., Experimental onchocercal keratitis. *Parasitol. Today*, 12:261–67, 1996.
4. Pearlman et al., The role of eosinophils and neutrophils in helminth-induced keratitis. *Inv. Ophthamol. Vis. Sci.*, 39:1176–82, 1998.
5. The Filarial Genome Project. Deep within the filarial genome: An update on the progress of the filarial genome project. *Parasitol. Today*, 15:219–24, 1999.
6. Lu et al., Sequence analysis and antigenic cross-reactivity of a venom allergen, antigen 5, from hornets, wasps, and yellow jackets. *J. Immunol.*, 150:2823–30, 1993.
7. Hawdon et al., Cloning and characterization of Ancylostoma-secreted protein. A novel protein associated with the transition to parasitism by infective hookworm larvae. *J. Biol. Chem.*, 271:6672–78, 1996.
8. Foster and Gerton, Autoantigen 1 of the guinea pig sperm acrosome is the homologue of mouse Tpx-1 and human Tpx-1 and is a member of the cysteine-rich secretory protein (CRISP) family. *Mol. Reprod. Dev.*, 44:221–29, 1996.
9. King and Lu, Hornet venom allergen antigen 5, Dol m 5: its T-cell epitopes in mice and its antigenic cross-reactivity with a mammalian testis protein. *J. Allergy Clin. Immunol.*, 99:630–39, 1997.
10. King and Valentine, Allergens of hymenopteran venoms. *Clin. Rev. Allergy*, 5:137–48, 1987.
11. Wilson et al., The Onchocerca volvulus homologue of the multifunctional polypeptide protein disulfide isomerase. *Mol. Biochem. Parasitol.*, 68:103–17, 1994.
12. Joseph et al., Onchocerca volvulus: Characterization of a highly immunogenic Gln-rich protein. *Mol. Biochem. Parasitol.*, 90:55–68, 1997.
13. Nielsen et al., Identification of prokaryotic and eukaryotic signal peptides and prediction of their cleavage sites. *Prot. Eng.*, 10:1–6, 1997.
14. Karlin and Altschul, Applications and statistics for multiple high-scoring segments in molecular sequences. *Proc. Nat. Acad. Sci. USA*, 90:5873–77, 1993.
15. Swofford, D. L., PAUP: *Phylogenetic Analysis Using Parsimony*. (Sunderland, MA: Sinauer Associates, 1998).
16. Kenyon et al., A model of angiogenesis in the mouse cornea. *Inv. Ophthamol. Vis. Sci.*, 37:1625–32, 1996.
17. Hoffman, D. R., Allergens in Hymenoptera venom. XXV: The amino acid sequences of antigen 5 molecules and the structural basis of antigenic cross-reactivity. *J. Allergy Clin. Immunol.*, 92:707–16, 1993.
18. Pearlman et al., Identification of an epitope of a recombinant *Onchocerca volvulus* protein that induces corneal pathology. *Mol. Biochem. Parasitol.*, 89:123–35, 1997.
19. Pearlman et al., Induction of Stromal Keratitis by Recombinant *Onchocerca volvulus* proteins Ov33, RAL2 and RAL6. *In Advances in Ocular Immunology*, R. B. Nussenblatt, S. M. Whitcup, R. R. Caspi, and I. Gery, eds. (Amsterdam: Elsevier, 1994) 289–92.
20. Smith et al., Vascular perfusion of Onchocerca volvulus nodules. *Trop. Med. Parasitol.*, 39 (Suppl. 4):418–21, 1988.
21. Folkman, J., Fighting cancer by attacking its blood supply. *Sci. Am.*, 275:150–54, 1996.
22. Polverini, P. J., The pathophysiology of angiogenesis. *Crit. Rev. Oral Biol.* Med., 6:230–47, 1995.
23. Battegay, E. J., Angiogenesis: mechanistic insights, neovascular diseases, and therapeutic prospects. *J. Mol. Med.*, 73:333–46, 1995.
24. Chaplain and Anderson, Mathematical modelling, simulation and prediction of tumour-induced angiogenesis. *Invasion Metastasis*, 16:222–34, 1996.
25. Arbiser, J. L., Angiogenesis and the skin: a primer. *J. Am. Acad. Dermatol.*, 34:486–97, 1996.
26. Colville-Nash and Willoughby, Growth factors in angiogenesis: current interest and therapeutic potential. *Mol. Med. Today*, 3:14–23, 1997.
27. Norrby, K., Angiogenesis: new aspects relating to its initiation and control. *APMIS*, 105:417–37, 1997.
28. Iruela-Arispe and Dvorak, Angiogenesis: a dynamic balance of stimulators and inhibitors. *Thromb. Haemost.*, 78:672–77, 1997.
29. Bhujwalla et al., Tumor angiogenesis, vascularization, and contrast-enhanced magnetic resonance imaging. *Top Magn. Reson. Imaging*, 10:92–103, 1999.
30. Paper, D. H., Natural products as angiogenesis inhibitors. *Planta. Med.*, 64:686–95, 1998.
31. Beers and Berkow, eds., *The Merck Manual of Diagnosis and Therapy*, 17th ed. (Whitehouse Station, NJ: Merck Research Laboratories, 1999) 1682–88.
32. Kennedy et al., The Ov20 protein of the parasitic nematode Onchocerca volvulus. A structurally novel class of small helix-rich retinol-binding proteins. *J. Biol. Chem.*, 21:29442–48, 1997.
33. Holst and Zipfel, A zinc finger gene from Onchocerca volvulus encodes a protein with a functional signal peptide and an unusual Ser-His finger motif. *J. Biol. Chem.*, 12:16725–33, 1996.

All publications mentioned hereinabove are hereby incorporated in their entirety. While the foregoing invention has been described in some detail for purposes of clarity and understanding, it will be appreciated by one skilled in the art, from a reading of the disclosure, that various changes in form and detail can be made without departing from the true scope of the invention in the appended claims.

What is claimed is:

1. A method for inducing angiogenesis in a tissue, comprising contacting the tissue with an amount of an isolated and purified *Onchocera volvulus* activation-associated protein (Ov-ASP) effective to induce angiogenesis in the tissue, wherein the Ov-ASP is Ov-ASP1 (SEQ ID NO:1) or Ov-ASP2 (SEQ ID NO:2), wherein said protein is isolated and purified such that it is free of other antigens from *Onchocera volvulus*.

2. The method of claim 1, wherein the Ov-ASP to protein is introduced to the tissue intradermally, intramuscularly, intraperitoneally, intravenously, subcutaneously, or topically.

3. The method of claim 1, wherein the tissue is selected from the group consisting of cardiac, cerebrovascular, endothelial, epithelial, fibrous, muscular, transplanted, vascular, vesicular, and wounded tissue.

4. The method of claim 3, wherein the tissue is associated with diseases or conditions selected from the group consisting of circulatory disorders, congenital heart disease, ischemia, myocardial disease, myocardial ischemic disorders, pericardial disease, and vascular disorders.

5. The method of claim 4, wherein the ischemia is cerebrovascular ischemia, myocardial ischemia, or veno-occlusive disease.

6. The method of claim 5, wherein the myocardial ischemia is coronary artery disease.

7. A method for inducing angiogenesis in a tissue, comprising introducing to the tissue a nucleic acid encoding an *Onchocerca volvulus* activation-associated secreted protein (Ov-ASP) in a manner permitting expression of an amount of the Ov-ASP effective to induce angiogenesis in the tissue, wherein the Ov-ASP is Ov-ASP1 (SEQ ID NO:1), or Ov-ASP2 (SEQ ID NO:2).

8. The method of claim 7, wherein the nucleic acid is introduced by electroporation, DEAE Dextran transfection, calcium phosphate transfection, cationic liposome fusion, protoplast fusion, DNA-coated microprojectile bombardment, injection with recombinant replication-defective viruses, viral vectors, or naked DNA transfer.

9. The method of claim 7, wherein the tissue is selected from the group consisting of cardiac, cerebrovascular, endothelial, epithelial, fibrous, muscular, transplanted, vascular, vesicular, and wounded tissue.

10. The method of claim 9, wherein the tissue is associated with diseases or conditions selected from the group consisting of circulatory disorders, congenital heart disease, ischemia, myocardial disease, myocardial ischemic disorders, pericardial disease, and vascular disorders.

11. The method of claim 10, wherein the ischemia is cerebrabascular ischemia, myocardial ischemia, or veno-occlusive disease.

12. The method of claim 11, wherein the myocardial ischemia is coronary artery disease.

* * * * *

SEQUENCE LISTING

<160> NUMBER OF SEQ ID NOS: 21

<210> SEQ ID NO 1
<211> LENGTH: 223
<212> TYPE: PRT
<213> ORGANISM: Onchocerca volvulus

<400> SEQUENCE: 1

-continued

```
Met Ile Leu Phe Ile Ile Phe Pro Ala Ile Val Val Ala Val Thr Gly
1               5                   10                  15

Tyr Asn Cys Pro Gly Gly Lys Leu Thr Ala Leu Glu Arg Lys Lys Ile
            20                  25                  30

Val Gly Gln Asn Asn Lys Tyr Arg Ser Asp Leu Ile Asn Gly Lys Leu
        35                  40                  45

Lys Asn Arg Asn Gly Thr Tyr Met Pro Arg Gly Lys Asn Met Leu Glu
    50                  55                  60

Leu Arg Trp Asp Cys Lys Leu Glu Ser Ser Ala Gln Arg Trp Ala Asn
65                  70                  75                  80

Gln Cys Ile Phe Gly His Ser Pro Arg Gln Gln Arg Glu Gly Val Gly
                85                  90                  95

Glu Asn Val Tyr Ala Tyr Trp Ser Ser Val Ser Val Glu Gly Leu Lys
            100                 105                 110

Lys Thr Ala Gly Thr Asp Ala Gly Lys Ser Trp Trp Ser Glu Leu Pro
        115                 120                 125

Lys Leu Tyr Glu Asn Asn Pro Ser Asn Asn Met Thr Trp Lys Val Ala
    130                 135                 140

Gly Gln Gly Val Leu His Phe Thr Gln Met Ala Trp Gly Lys Thr Tyr
145                 150                 155                 160

Lys Ile Gly Cys Gly Val Ala Thr Gln Cys Asp Gly Gly Arg Thr Leu
                165                 170                 175

Ile Val Ile Cys His Tyr Ser Pro Gly Gly Asn Met Val Gly Glu Val
            180                 185                 190

Ile Tyr Gln Arg Gly Asn Pro Cys Asn Pro Cys Lys Val Asp Lys Asp
        195                 200                 205

Cys Tyr Thr Lys Lys Cys Leu Ser Lys Ser Gly Leu Cys Arg Lys
    210                 215                 220


<210> SEQ ID NO 2
<211> LENGTH: 253
<212> TYPE: PRT
<213> ORGANISM: Onchocerca volvulus

<400> SEQUENCE: 2

Met Ile Leu Phe Leu Ile Phe Pro Ala Ile Ile Val Ala Val Thr Gly
1               5                   10                  15

Tyr Asp Cys Tyr Arg Gly Lys Leu Thr Pro Gln Tyr Arg Glu Lys Ile
            20                  25                  30

Val Arg Glu His Asn Arg Leu Arg Ser Lys Leu Ala Lys Gly Thr Tyr
        35                  40                  45

Lys Asn Ser Ala Gly Lys Trp Met Pro Lys Gly Lys Asn Met Met Glu
    50                  55                  60

Met Lys Trp Asp Cys Glu Leu Glu Leu Met Ala Gln Arg Trp Ala Asp
65                  70                  75                  80

Gln Cys Val Ser Gly Asn Ser Pro Lys Asp Arg Arg Gly Arg Ile Gly
                85                  90                  95

Glu Asn Val Tyr Thr Gln Arg Ser Asp Thr Ser Val Ala Val Tyr Gly
            100                 105                 110

Thr Ser Gly Ile Met Ile Ala Leu Glu Ser Trp Trp Val Glu Leu Thr
        115                 120                 125

Arg Ser Tyr Lys Asn Asn Pro Ser Asn Lys Tyr Thr Ser Ile Val Ala
    130                 135                 140

Asn Arg Gly Val Ser Asn Phe Thr Gln Leu Ala Trp Gly Lys Thr Tyr
```

-continued

```
145                 150                 155                 160

Lys Val Gly Cys Gly Ile Ala Thr His Cys Asp Gly Gly Lys Ala Phe
                165                 170                 175

Val Ala Val Cys Gln Tyr Asn Pro Gly Gly Asn Thr Met Gly Glu Ser
            180                 185                 190

Ile Tyr Glu Lys Gly Arg Pro Cys Lys Thr Asp Arg Asp Cys Ser Ser
        195                 200                 205

Arg Lys Cys Cys Lys Arg Ile Trp Ile Val Gln Ile Glu Phe Leu His
    210                 215                 220

Leu Ile Phe Gly Phe Ala Met His Pro Tyr Ile Tyr Phe Ser Ala Lys
225                 230                 235                 240

Lys Leu Lys Lys Ile Phe Ile Ile Lys Tyr Glu Tyr Ile
                245                 250


<210> SEQ ID NO 3
<211> LENGTH: 220
<212> TYPE: PRT
<213> ORGANISM: Onchocerca volvulus

<400> SEQUENCE: 3

Met Ile Leu Phe Ile Ile Phe Pro Ala Ile Ile Val Ala Val Thr Gly
1               5                   10                  15

His Asp Cys His Arg Gly Lys Leu Thr Ser Leu Gln Arg Asp Ile Ile
            20                  25                  30

Tyr Asp Glu His Asn Lys Tyr Arg Ser Arg Leu Val Lys Gly Asn Phe
        35                  40                  45

Ala Asn Lys Asp Gly Asn Ser Met Pro Lys Gly Lys Asn Met Met Glu
    50                  55                  60

Met Glu Trp Asp Cys Glu Leu Glu Ile Ser Ala Gln Asn Trp Ala Asp
65                  70                  75                  80

Gln Cys Ile Phe Gly Tyr Ser Pro Glu Asn Gln Arg Glu Gly Val Gly
                85                  90                  95

Glu Asn Ile Tyr Ala Leu Gly Leu Pro Lys Asp Val Glu Val Phe Asn
            100                 105                 110

Thr Ser Ala Ala Leu Phe Ala Ile Glu Ser Trp Trp Thr Glu Leu Ile
        115                 120                 125

Arg Ser Tyr Arg Asn Asn Pro Ser Asn Lys Leu Thr Ser Ser Val Ala
    130                 135                 140

Ser Gln Asp Val Leu His Phe Thr Gln Met Ala Trp Gly Lys Thr His
145                 150                 155                 160

Lys Val Gly Cys Gly Ile Ala Met His Cys Asp Asp Gly Glu Ala Phe
                165                 170                 175

Ile Val Val Cys His Tyr Ala Pro Arg Gly Asn Thr Ile Gly Glu Leu
            180                 185                 190

Ile Tyr Glu Gln Gly Ser Pro Cys Lys Val Asn Lys His Cys Arg Thr
        195                 200                 205

Lys Lys Cys Ser Arg Lys Ser Gly Leu Cys Lys Lys
    210                 215                 220


<210> SEQ ID NO 4
<211> LENGTH: 220
<212> TYPE: PRT
<213> ORGANISM: Brugia malayi

<400> SEQUENCE: 4

Met Leu Phe Phe Val Ile Phe Ser Ile Thr Ile Ala Val Val Ala Gly
```

-continued

```
1               5                   10                  15

Phe Glu Cys Pro Gly Gly Arg Leu Thr Pro Gln Gln Arg Lys Asp Ile
            20                  25                  30

Val Arg Gln Asn Asn Lys Phe Arg Ser Leu Leu Ile His Gly Lys Leu
        35                  40                  45

Lys Asn Arg Asn Gly Thr Tyr Met Pro Arg Gly Lys Asn Met Leu Leu
    50                  55                  60

Leu Lys Trp Ser Cys Gln Leu Glu Asn Ser Ala Gln Arg Trp Ala Asn
65                  70                  75                  80

Gln Cys Val Phe Gly His Ser Pro Arg Asn Gln Arg Gln Gly Ile Gly
                85                  90                  95

Glu Asn Val Tyr Ala Tyr Trp Ser Ser Glu Ser Val Glu Lys Leu Arg
            100                 105                 110

Asn Thr Ala Gly Thr Glu Ala Gly Lys Ser Trp Trp Ser Glu Phe Pro
        115                 120                 125

Lys Leu Tyr Lys Gln Asn Pro Ser Asn Asn Leu Thr Asp Asp Val Ala
    130                 135                 140

Arg Gln Gly Val Leu His Phe Thr Gln Met Ala Trp Gly Lys Thr His
145                 150                 155                 160

Lys Ile Gly Cys Gly Ile Ala Thr Asn Cys Asp Gly Gly Arg Thr Leu
                165                 170                 175

Ile Ala Ile Cys His Tyr Ser Pro Ala Gly Asn Met Leu Lys Glu Leu
            180                 185                 190

Ile Tyr Glu Leu Gly Glu Pro Cys Lys Thr Asp Ser Asp Cys Asn Thr
        195                 200                 205

Lys Lys Cys Ala Lys Lys Ser Gly Leu Cys Arg Lys
    210                 215                 220


<210> SEQ ID NO 5
<211> LENGTH: 192
<212> TYPE: PRT
<213> ORGANISM: Ancylostoma caninum

<400> SEQUENCE: 5

Met Thr Asp Ser Val Arg Asp Thr Phe Leu Ser Val His Asn Glu Phe
1               5                   10                  15

Arg Ser Ser Val Ala Arg Gly Leu Glu Pro Asp Ala Leu Gly Gly Asn
            20                  25                  30

Ala Pro Lys Ala Ala Lys Met Leu Lys Met Val Tyr Asp Cys Glu Val
        35                  40                  45

Glu Ala Ser Ala Ile Arg His Gly Asn Lys Cys Val Tyr Gln His Ser
    50                  55                  60

His Gly Glu Asp Arg Pro Gly Leu Gly Glu Asn Ile Tyr Lys Thr Ser
65                  70                  75                  80

Val Leu Lys Phe Asp Lys Asn Lys Ala Ala Lys Gln Ala Ser Gln Leu
                85                  90                  95

Trp Trp Asn Glu Leu Lys Glu Phe Gly Val Gly Pro Ser Asn Val Leu
            100                 105                 110

Thr Thr Ala Leu Trp Asn Arg Pro Gly Met Gln Ile Gly His Tyr Thr
        115                 120                 125

Gln Met Ala Trp Asp Thr Thr Tyr Lys Leu Gly Cys Ala Val Val Phe
    130                 135                 140

Cys Asn Asp Phe Thr Phe Gly Val Cys Gln Tyr Gly Pro Gly Gly Asn
145                 150                 155                 160
```

-continued

```
Tyr Met Gly His Val Ile Tyr Thr Met Gly Gln Pro Cys Ser Gln Cys
                165                 170                 175

Ser Pro Gly Ala Thr Cys Ser Val Thr Glu Gly Leu Cys Ser Ala Pro
            180                 185                 190


<210> SEQ ID NO 6
<211> LENGTH: 227
<212> TYPE: PRT
<213> ORGANISM: Vespula vulgarus

<400> SEQUENCE: 6

Met Glu Ile Ser Gly Leu Val Tyr Leu Ile Ile Ile Val Thr Ile Ile
1               5                   10                  15

Asp Leu Pro Tyr Gly Lys Ala Asn Asn Tyr Cys Lys Ile Lys Cys Leu
            20                  25                  30

Lys Gly Gly Val His Thr Ala Cys Lys Tyr Gly Ser Leu Lys Pro Asn
        35                  40                  45

Cys Gly Asn Lys Val Val Val Ser Tyr Gly Leu Thr Lys Gln Glu Lys
    50                  55                  60

Gln Asp Ile Leu Lys Glu His Asn Asp Phe Arg Gln Lys Ile Ala Arg
65                  70                  75                  80

Gly Leu Glu Thr Arg Gly Asn Pro Gly Pro Gln Pro Pro Ala Lys Asn
                85                  90                  95

Met Lys Asn Leu Val Trp Asn Asp Glu Leu Ala Tyr Val Ala Gln Val
            100                 105                 110

Trp Ala Asn Gln Cys Gln Tyr Gly His Asp Thr Cys Arg Asp Val Ala
        115                 120                 125

Lys Tyr Gln Val Gly Gln Asn Val Ala Leu Thr Gly Ser Thr Ala Ala
    130                 135                 140

Lys Tyr Asp Asp Pro Val Lys Leu Val Lys Met Trp Glu Asp Glu Val
145                 150                 155                 160

Lys Asp Tyr Asn Pro Lys Lys Lys Phe Ser Gly Asn Asp Phe Leu Lys
                165                 170                 175

Thr Gly His Tyr Thr Gln Met Val Trp Ala Asn Thr Lys Glu Val Gly
            180                 185                 190

Cys Gly Ser Ile Lys Tyr Ile Gln Glu Lys Trp His Lys His Tyr Leu
        195                 200                 205

Val Cys Asn Tyr Gly Pro Ser Gly Asn Phe Met Asn Glu Glu Leu Tyr
    210                 215                 220

Gln Thr Lys
225


<210> SEQ ID NO 7
<211> LENGTH: 243
<212> TYPE: PRT
<213> ORGANISM: Homo sapiens

<400> SEQUENCE: 7

Met Ala Leu Leu Pro Val Leu Phe Leu Val Thr Val Leu Leu Pro Ser
1               5                   10                  15

Leu Pro Ala Glu Gly Lys Asp Pro Ala Phe Thr Ala Leu Leu Thr Thr
            20                  25                  30

Gln Leu Gln Val Gln Arg Glu Ile Val Asn Lys His Asn Glu Leu Arg
        35                  40                  45

Lys Ala Val Ser Pro Pro Ala Ser Asn Met Leu Lys Met Glu Trp Ser
    50                  55                  60
```

-continued

```
Arg Glu Val Thr Thr Asn Ala Gln Arg Trp Ala Asn Lys Cys Thr Leu
65                  70                  75                  80

Gln His Ser Asp Pro Glu Asp Arg Lys Thr Ser Thr Arg Cys Gly Glu
                85                  90                  95

Asn Leu Tyr Met Ser Ser Asp Pro Thr Ser Trp Ser Ser Ala Ile Gln
            100                 105                 110

Ser Trp Tyr Asp Glu Ile Leu Asp Phe Val Tyr Gly Val Gly Pro Lys
        115                 120                 125

Ser Pro Asn Ala Val Val Gly His Tyr Thr Gln Leu Val Trp Tyr Ser
    130                 135                 140

Thr Tyr Gln Val Gly Cys Gly Ile Ala Tyr Cys Pro Asn Gln Asp Ser
145                 150                 155                 160

Leu Lys Tyr Tyr Tyr Val Cys Gln Tyr Cys Pro Ala Gly Asn Asn Met
                165                 170                 175

Asn Arg Lys Asn Thr Pro Tyr Gln Gln Gly Thr Pro Cys Ala Gly Cys
            180                 185                 190

Pro Asp Asp Cys Asp Lys Gly Leu Cys Thr Asn Ser Cys Gln Tyr Gln
        195                 200                 205

Asp Leu Leu Ser Asn Cys Asp Ser Leu Lys Asn Thr Ala Gly Cys Glu
    210                 215                 220

His Glu Leu Leu Lys Glu Lys Cys Lys Ala Thr Cys Leu Cys Glu Asn
225                 230                 235                 240

Lys Ile Tyr


<210> SEQ ID NO 8
<211> LENGTH: 31
<212> TYPE: DNA
<213> ORGANISM: artificial sequence
<220> FEATURE:
<221> NAME/KEY: primer_bind
<222> LOCATION: (1)..(31)
<223> OTHER INFORMATION: primer flanking complete open reading frame of
      Ov-asp-1 clone

<400> SEQUENCE: 8

ggaattccat atgatacttt tcatcatctt c                                31


<210> SEQ ID NO 9
<211> LENGTH: 21
<212> TYPE: DNA
<213> ORGANISM: artificial sequence
<220> FEATURE:
<221> NAME/KEY: primer_bind
<222> LOCATION: (1)..(21)
<223> OTHER INFORMATION: primer flanking complete open reading frame of
      Ov-asp-1 clone

<400> SEQUENCE: 9

tcattttctg cacagtccag a                                           21


<210> SEQ ID NO 10
<211> LENGTH: 30
<212> TYPE: DNA
<213> ORGANISM: artificial sequence
<220> FEATURE:
<221> NAME/KEY: primer_bind
<222> LOCATION: (1)..(30)
<223> OTHER INFORMATION: primer flanking complete open reading frame of
      Ov-asp-2 clone

<400> SEQUENCE: 10

ggattccata tgatactttt tctcatcttc                                  30
```

<210> SEQ ID NO 11
<211> LENGTH: 25
<212> TYPE: DNA
<213> ORGANISM: artificial sequence
<220> FEATURE:
<221> NAME/KEY: primer_bind
<222> LOCATION: (1)..(25)
<223> OTHER INFORMATION: primer flanking complete open reading frame of
      Ov-asp-2 clone

<400> SEQUENCE: 11
cataataact actaaatata tacgt                                           25

<210> SEQ ID NO 12
<211> LENGTH: 31
<212> TYPE: DNA
<213> ORGANISM: artificial sequence
<220> FEATURE:
<221> NAME/KEY: primer_bind
<222> LOCATION: (1)..(31)
<223> OTHER INFORMATION: primer flanking complete open reading frame of
      Ov-asp-3 clone

<400> SEQUENCE: 12
ggaattccat atgatacttt tcatcatctt c                                    31

<210> SEQ ID NO 13
<211> LENGTH: 21
<212> TYPE: DNA
<213> ORGANISM: artificial sequence
<220> FEATURE:
<221> NAME/KEY: primer_bind
<222> LOCATION: (1)..(21)
<223> OTHER INFORMATION: primer flanking complete open reading frame of
      Ov-asp-3 clone

<400> SEQUENCE: 13
tcattttttg cacaatccag a                                               21

<210> SEQ ID NO 14
<211> LENGTH: 17
<212> TYPE: DNA
<213> ORGANISM: artificial sequence
<220> FEATURE:
<221> NAME/KEY: primer_bind
<222> LOCATION: (1)..(17)
<223> OTHER INFORMATION: gene-specific primer used to amplify Ov-asp-1
      clone

<400> SEQUENCE: 14
aaaactgctg gtacgga                                                    17

<210> SEQ ID NO 15
<211> LENGTH: 23
<212> TYPE: DNA
<213> ORGANISM: artificial sequence
<220> FEATURE:
<221> NAME/KEY: primer_bind
<222> LOCATION: (1)..(23)
<223> OTHER INFORMATION: gene-specific primer used to amplify Ov-asp-1
      clone

<400> SEQUENCE: 15
cgagaattaa atgaagaaaa gcg                                             23

<210> SEQ ID NO 16
<211> LENGTH: 23

-continued

```
<212> TYPE: DNA
<213> ORGANISM: artificial sequence
<220> FEATURE:
<221> NAME/KEY: primer_bind
<222> LOCATION: (1)..(23)
<223> OTHER INFORMATION: gene-specific primer used to amplify Ov-asp-2
      clone

<400> SEQUENCE: 16

gtttacaccc agcggtcaga tac                                              23


<210> SEQ ID NO 17
<211> LENGTH: 30
<212> TYPE: DNA
<213> ORGANISM: artificial sequence
<220> FEATURE:
<221> NAME/KEY: primer_bind
<222> LOCATION: (1)..(30)
<223> OTHER INFORMATION: gene-specific primer used to amplify Ov-asp-2
      clone

<400> SEQUENCE: 17

ccaaaaatta aatgaagaaa ttcaatttgc                                       30


<210> SEQ ID NO 18
<211> LENGTH: 23
<212> TYPE: DNA
<213> ORGANISM: artificial sequence
<220> FEATURE:
<221> NAME/KEY: primer_bind
<222> LOCATION: (1)..(23)
<223> OTHER INFORMATION: gene-specific primer used to amplify Ov-asp-3
      clone

<400> SEQUENCE: 18

cgccttaggg ttaccaaaag atg                                              23


<210> SEQ ID NO 19
<211> LENGTH: 23
<212> TYPE: DNA
<213> ORGANISM: artificial sequence
<220> FEATURE:
<221> NAME/KEY: primer_bind
<222> LOCATION: (1)..(23)
<223> OTHER INFORMATION: gene-specific primer used to amplify Ov-asp-3
      clone

<400> SEQUENCE: 19

caaaaattaa atgaagtgaa acg                                              23


<210> SEQ ID NO 20
<211> LENGTH: 20
<212> TYPE: DNA
<213> ORGANISM: artificial sequence
<220> FEATURE:
<221> NAME/KEY: primer_bind
<222> LOCATION: (1)..(20)
<223> OTHER INFORMATION: gene-specific primer used to amplify cDNA
      encoding glycolytic enzyme Ov-gpd-1

<400> SEQUENCE: 20

tgatctcact tgccgactgc                                                  20


<210> SEQ ID NO 21
<211> LENGTH: 18
<212> TYPE: DNA
<213> ORGANISM: artificial sequence
<220> FEATURE:
<221> NAME/KEY: primer_bind
```

-continued

```
<222> LOCATION: (1)..(18)
<223> OTHER INFORMATION: gene-specific primer used to amplify cDNA
      encoding glycolytic enzyme Ov-gpd-1

<400> SEQUENCE: 21

aaggtgttgt cagaaggc                                                18
```